US009453850B2

(12) United States Patent
Sturman et al.

(10) Patent No.: US 9,453,850 B2
(45) Date of Patent: Sep. 27, 2016

(54) ELECTRONIC ANALYTE ASSAYING DEVICE

(71) Applicant: Church & Dwight, Co., Inc., Princeton, NJ (US)

(72) Inventors: Andy Sturman, San Diego, CA (US); Benedict Zin, San Diego, CA (US); Albert Nazareth, Mercerville, NJ (US); Henry Bell, Hamilton Square, NJ (US)

(73) Assignee: CHURCH & DWIGHT CO., INC., Princeton, NJ (US)

( * ) Notice: Subject to any disclaimer, the term of this patent is extended or adjusted under 35 U.S.C. 154(b) by 120 days.

(21) Appl. No.: 14/453,918

(22) Filed: Aug. 7, 2014

(65) Prior Publication Data

US 2015/0017068 A1      Jan. 15, 2015

Related U.S. Application Data

(62) Division of application No. 12/967,971, filed on Dec. 14, 2010, now Pat. No. 8,828,329.

(60) Provisional application No. 61/389,050, filed on Oct. 1, 2010.

(51) Int. Cl.
*G01N 21/03* (2006.01)
*G01N 33/68* (2006.01)
*G01N 21/84* (2006.01)
(Continued)

(52) U.S. Cl.
CPC ............ *G01N 33/689* (2013.01); *G01N 21/17* (2013.01); *G01N 21/8483* (2013.01); *G01N 33/493* (2013.01); *G01N 33/62* (2013.01); *G01N 33/76* (2013.01)

(58) Field of Classification Search
None
See application file for complete search history.

(56) References Cited

U.S. PATENT DOCUMENTS 4,203,724 A    5/1980  Sawai et al.
4,859,612 A    8/1989  Cole et al.
(Continued)

FOREIGN PATENT DOCUMENTS

EP          439893 A2    8/1991
GB         2460660 A     9/2009
(Continued)

OTHER PUBLICATIONS

International Search Report and Written Opinion of PCT/US2011/052958, mailed Feb. 7, 2012, which corresponds to this current application.
(Continued)

*Primary Examiner* — Robert Xu
(74) *Attorney, Agent, or Firm* — Knobbe Martens

(57) ABSTRACT

An improved electronic diagnostic device for detecting the presence of an analyte in a fluid sample comprises a casing having a display, a test strip mounted in the casing, a processor mounted in the casing, and a first sensor mounted in the casing and operatively coupled to the processor. The processor is configured to receive a signal from the first sensor when the device is exposed to ambient light thereby causing the device to become activated. The device includes a light shield that exerts pressure across a width of the test strip to prevent fluid channeling along the length of the test strip. The processor is configured to present an early positive test result reading when a measured value exceeds a predetermined early reading threshold value at any time after a predetermined early testing time period.

4 Claims, 13 Drawing Sheets

(51) Int. Cl.
  *G01N 21/17* (2006.01)
  *G01N 33/493* (2006.01)
  *G01N 33/62* (2006.01)
  *G01N 33/76* (2006.01)

(56) References Cited

U.S. PATENT DOCUMENTS

| | | |
|---|---|---|
| 4,865,028 A | 9/1989 | Swart et al. |
| 4,916,056 A | 4/1990 | Brown et al. |
| 4,956,302 A | 9/1990 | Gordon et al. |
| 5,008,080 A | 4/1991 | Brown et al. |
| 5,017,471 A | 5/1991 | Fellman |
| 5,032,506 A | 7/1991 | Palmer et al. |
| 5,036,000 A | 7/1991 | Palmer et al. |
| 5,073,482 A | 12/1991 | Goldstein |
| 5,075,078 A | 12/1991 | Osikowicz et al. |
| 5,103,836 A | 4/1992 | Goldstein et al. |
| 5,112,741 A | 5/1992 | Palmer et al. |
| 5,112,758 A | 5/1992 | Fellman et al. |
| 5,116,125 A | 5/1992 | Rigler et al. |
| 5,120,643 A | 6/1992 | Ching et al. |
| 5,126,247 A | 6/1992 | Palmer et al. |
| 5,141,850 A | 8/1992 | Cole et al. |
| 5,145,789 A | 9/1992 | Corti et al. |
| 5,149,622 A | 9/1992 | Brown et al. |
| 5,160,701 A | 11/1992 | Brown et al. |
| 5,232,914 A | 8/1993 | Fellman et al. |
| 5,242,804 A | 9/1993 | Bahar et al. |
| 5,296,375 A | 3/1994 | Kricka et al. |
| 5,335,673 A | 8/1994 | Goldstein et al. |
| 5,339,829 A | 8/1994 | Thieme et al. |
| 5,366,863 A | 11/1994 | Clough et al. |
| 5,418,136 A | 5/1995 | Miller et al. |
| 5,466,587 A | 11/1995 | Fitzpatrick-McElligott et al. |
| 5,468,648 A | 11/1995 | Chandler et al. |
| 5,479,937 A | 1/1996 | Thieme et al. |
| 5,573,009 A | 11/1996 | Thieme et al. |
| 5,577,512 A | 11/1996 | Caillouette et al. |
| 5,578,577 A | 11/1996 | Ching et al. |
| 5,580,794 A | 12/1996 | Allen |
| 5,602,040 A | 2/1997 | May et al. |
| 5,622,871 A | 4/1997 | May et al. |
| 5,656,503 A | 8/1997 | May et al. |
| 5,664,579 A | 9/1997 | Caillouette et al. |
| 5,695,929 A | 12/1997 | Goldstein et al. |
| D390,667 S | 2/1998 | Nazareth et al. |
| 5,714,341 A | 2/1998 | Thieme et al. |
| 5,714,389 A | 2/1998 | Charlton et al. |
| 5,735,801 A | 4/1998 | Caillouette et al. |
| 5,736,322 A | 4/1998 | Goldstein et al. |
| 5,738,634 A | 4/1998 | Caillouette et al. |
| 5,738,682 A | 4/1998 | Jensma |
| 5,739,041 A | 4/1998 | Nazareth et al. |
| 5,744,366 A | 4/1998 | Kricka et al. |
| 5,762,614 A | 6/1998 | Caillouette |
| 5,763,262 A | 6/1998 | Wong et al. |
| 5,827,200 A | 10/1998 | Caillouette |
| 5,830,154 A | 11/1998 | Goldstein et al. |
| 5,830,410 A | 11/1998 | Thieme et al. |
| 5,837,546 A | 11/1998 | Allen et al. |
| 5,846,835 A | 12/1998 | Sisbarro et al. |
| 5,849,713 A | 12/1998 | Eisenbach et al. |
| 5,859,374 A | 1/1999 | Mink et al. |
| 5,866,345 A | 2/1999 | Wilding et al. |
| 5,871,905 A | 2/1999 | Thieme et al. |
| 5,885,789 A | 3/1999 | Kardos et al. |
| 5,916,176 A | 6/1999 | Caillouette |
| 5,928,165 A | 7/1999 | Caillouette et al. |
| 5,989,921 A | 11/1999 | Charlton et al. |
| 5,998,161 A | 12/1999 | Caillouette |
| 6,013,036 A | 1/2000 | Caillouette et al. |
| 6,039,894 A | 3/2000 | Sanjurjo et al. |
| 6,046,057 A | 4/2000 | Nazareth |
| 6,069,011 A | 5/2000 | Riedel |
| 6,083,178 A | 7/2000 | Caillouette |
| 6,092,527 A | 7/2000 | Jensma |
| 6,117,090 A | 9/2000 | Caillouette |
| 6,175,752 B1 | 1/2001 | Say et al. |
| 6,187,598 B1 | 2/2001 | May et al. |
| 6,190,331 B1 | 2/2001 | Caillouette |
| 6,228,660 B1 | 5/2001 | May et al. |
| 6,277,650 B1 | 8/2001 | Nazareth |
| 6,283,927 B1 | 9/2001 | Caillouette |
| 6,303,081 B1 | 10/2001 | Mink et al. |
| 6,312,914 B1 | 11/2001 | Kardos et al. |
| 6,316,274 B1 | 11/2001 | Herron et al. |
| 6,319,676 B1 | 11/2001 | Nazareth |
| 6,352,862 B1 | 3/2002 | Davis et al. |
| 6,387,090 B1 | 5/2002 | Jensma |
| 6,390,991 B1 | 5/2002 | Caillouette |
| 6,391,654 B1 | 5/2002 | Bateman et al. |
| 6,402,705 B1 | 6/2002 | Caillouette |
| 6,409,680 B1 | 6/2002 | Caillouette |
| 6,409,681 B1 | 6/2002 | Caillouette |
| 6,445,451 B1 | 9/2002 | Douglas-Hamilton et al. |
| 6,472,226 B1 | 10/2002 | Barradine et al. |
| 6,485,982 B1 | 11/2002 | Charlton |
| D467,349 S | 12/2002 | Niedbala et al. |
| D470,240 S | 2/2003 | Niedbala et al. |
| 6,526,363 B2 | 2/2003 | Wilkinson et al. |
| 6,534,320 B2 | 3/2003 | Ching |
| 6,534,324 B1 | 3/2003 | Zin |
| 6,544,196 B2 | 4/2003 | Caillouette |
| 6,551,841 B1 | 4/2003 | Wilding et al. |
| D474,278 S | 5/2003 | Niedbala et al. |
| D474,280 S | 5/2003 | Niedbala et al. |
| D481,800 S | 11/2003 | Niedbala et al. |
| D491,274 S | 6/2004 | Dubniczki et al. |
| 6,750,962 B2 | 6/2004 | Douglas et al. |
| 6,753,189 B1 | 6/2004 | Narahara et al. |
| 6,767,714 B2 | 7/2004 | Nazareth et al. |
| 6,848,598 B2 | 2/2005 | Matthews et al. |
| 6,855,561 B2 | 2/2005 | Jerome et al. |
| 6,929,945 B2 | 8/2005 | Aravanis et al. |
| 7,002,088 B2 | 2/2006 | Shin et al. |
| 7,045,342 B2 | 5/2006 | Nazareth et al. |
| 7,108,966 B2 | 9/2006 | Aravanis et al. |
| 7,179,641 B2 | 2/2007 | Brickwood et al. |
| 7,179,657 B2 | 2/2007 | Jerome et al. |
| 7,192,555 B2 | 3/2007 | Mink et al. |
| 7,210,779 B2 | 5/2007 | Esser et al. |
| 7,211,403 B2 | 5/2007 | Barradine et al. |
| 7,214,542 B2 | 5/2007 | Hutchinson et al. |
| 7,220,597 B2 | 5/2007 | Zin et al. |
| 7,230,305 B2 | 6/2007 | Min et al. |
| 7,238,537 B2 | 7/2007 | Davis et al. |
| 7,239,394 B2 | 7/2007 | Sharrock et al. |
| 7,250,308 B2 | 7/2007 | Whiting et al. |
| D548,359 S | 8/2007 | Illein et al. |
| 7,297,502 B2 | 11/2007 | Gao et al. |
| 7,315,378 B2 | 1/2008 | Phelan et al. |
| 7,317,532 B2 | 1/2008 | Sharrock et al. |
| 7,326,578 B2 | 2/2008 | Bateman et al. |
| 7,384,796 B2 | 6/2008 | Davis et al. |
| 7,407,813 B2 | 8/2008 | Davis et al. |
| 7,476,548 B2 | 1/2009 | Blatt et al. |
| 7,499,170 B2 | 3/2009 | Sasaki et al. |
| 7,537,937 B2 | 5/2009 | Jerome et al. |
| 7,553,675 B2 | 6/2009 | Jerome et al. |
| 7,616,315 B2 | 11/2009 | Sharrock et al. |
| 7,622,729 B2 | 11/2009 | Duesbury |
| 7,670,853 B2 | 3/2010 | Jina et al. |
| 7,763,454 B2 | 7/2010 | Nazareth et al. |
| 7,772,578 B2 | 8/2010 | Duesbury et al. |
| 7,776,618 B2 | 8/2010 | Nazareth et al. |
| 7,799,275 B2 | 9/2010 | Duesbury et al. |
| 7,858,396 B2 | 12/2010 | Corstjens et al. |
| 8,038,668 B2 | 10/2011 | Scott et al. |
| 2002/0015663 A1 | 2/2002 | Goldstein et al. |
| 2002/0192839 A1 | 12/2002 | Mink et al. |
| 2005/0101032 A1 | 5/2005 | Blatt et al. |
| 2005/0158700 A1 | 7/2005 | Brickwood et al. |
| 2006/0029924 A1 | 2/2006 | Brewster et al. |
| 2006/0040405 A1 | 2/2006 | Charlton et al. |

(56) References Cited

U.S. PATENT DOCUMENTS

| | | |
|---|---|---|
| 2006/0110821 A1 | 5/2006 | Brickwood et al. |
| 2008/0261323 A1 | 10/2008 | Diamond et al. |
| 2010/0086933 A1 | 4/2010 | Hospach et al. |
| 2010/0126881 A1 | 5/2010 | Diamond et al. |
| 2010/0239460 A1 | 9/2010 | Nazareth |
| 2010/0240149 A1 | 9/2010 | Nazareth |
| 2010/0261293 A1 | 10/2010 | Nazareth et al. |
| 2010/0267166 A1 | 10/2010 | Nazareth et al. |
| 2011/0056264 A1 | 3/2011 | Kaplan et al. |
| 2011/0290673 A1 | 12/2011 | Diamond et al. |
| 2012/0015376 A1 | 1/2012 | Bornhop |

FOREIGN PATENT DOCUMENTS

| | | |
|---|---|---|
| WO | 9009592 A1 | 8/1990 |
| WO | 98/25143 A1 | 6/1998 |
| WO | 9958050 A1 | 11/1999 |
| WO | 0128101 A1 | 4/2001 |
| WO | 02/101343 A2 | 12/2002 |
| WO | 03000127 A2 | 1/2003 |

OTHER PUBLICATIONS

NanoFlexTM Valves—http://005c6c4.netsolhost.com/technology/nanoflex.html—pp. 1-3—retrieved from Internet, 2008.

Communication pursuant to Rule 164(1) EPC—Supplementary European Search Report for EP13752396.5 pp. 1-5, mailed Sep. 15, 2015, which is a counterpart to U.S. Appl. No. 13/402,024, which corresponds to this present application.

Extended European Search Report for EP13752396.5, pp. 1-15, mailed on Jan. 14, 2016, which is a counterpart to U.S. Appl. No. 13/402,024, which corresponds to this present application.

Patent Examinatin Report No. 1 for AU2013222512, pp. 1-3, mailed on Jan. 12, 2016, which is a counterpart to U.S. Appl. No. 13/402,024, which corresponds to this present application.

Non-Final Office Action, mailed Jan. 15, 2015 for U.S. Appl. No. 13/402,024, which corresponds to this present application.

Final Office Action mailed Sep. 25, 2015 for U.S. Appl. No. 13/402,024, which corresponds to this present application.

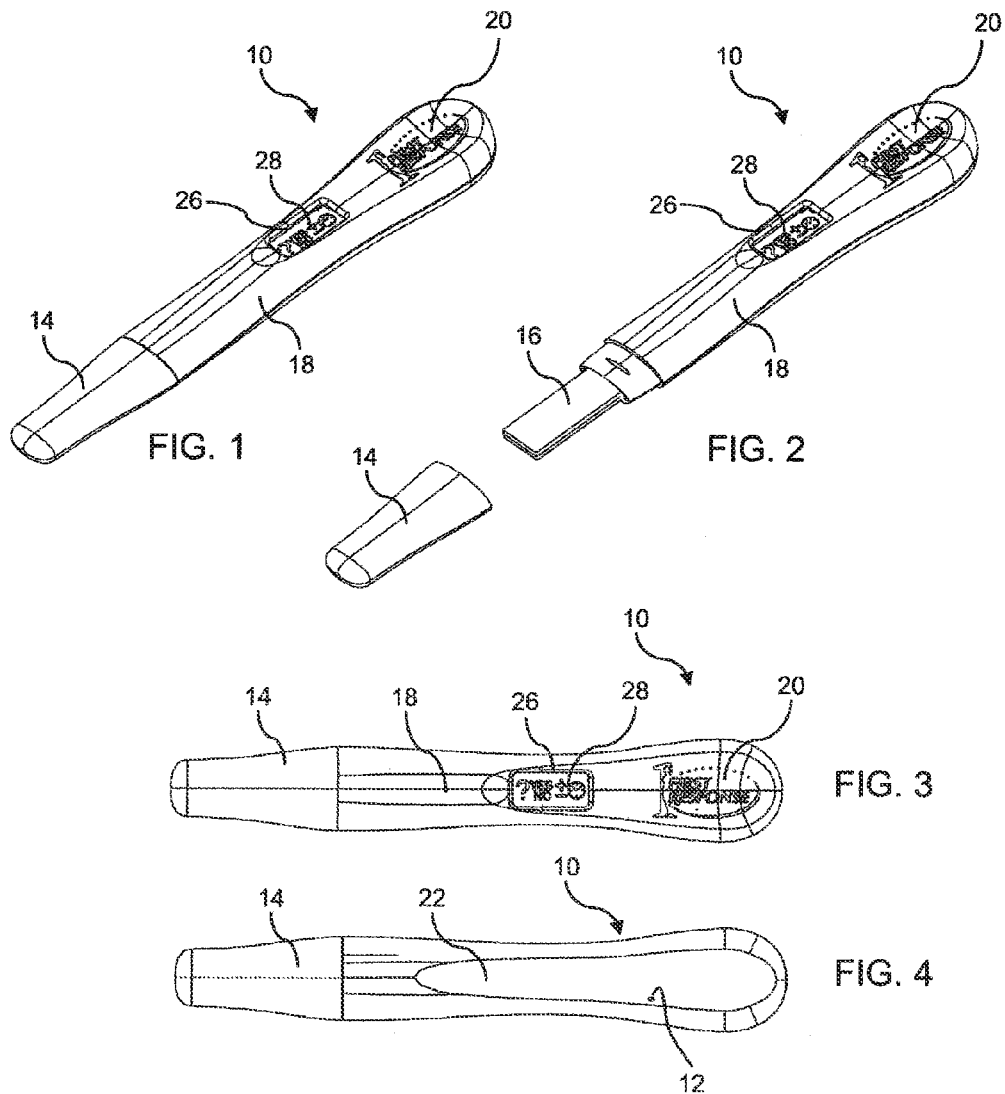

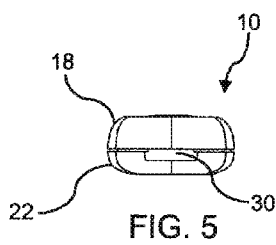
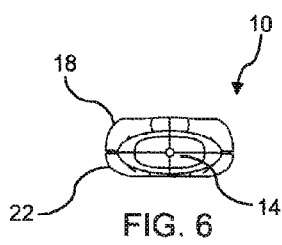
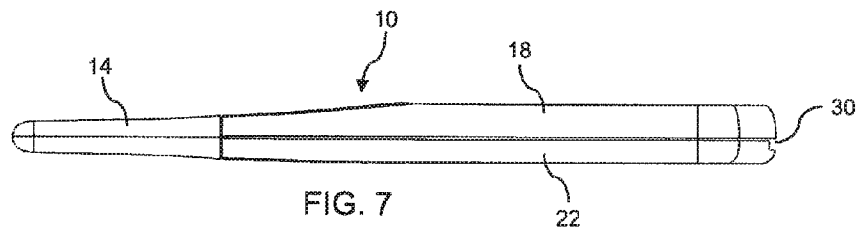
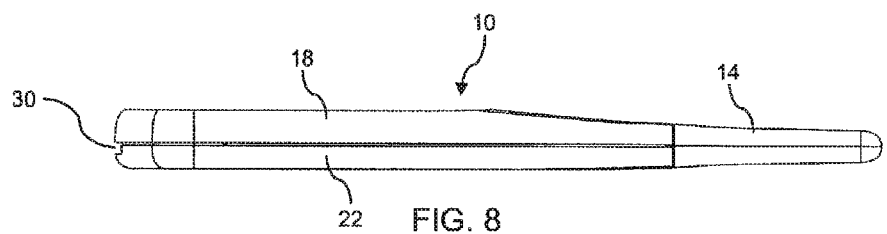

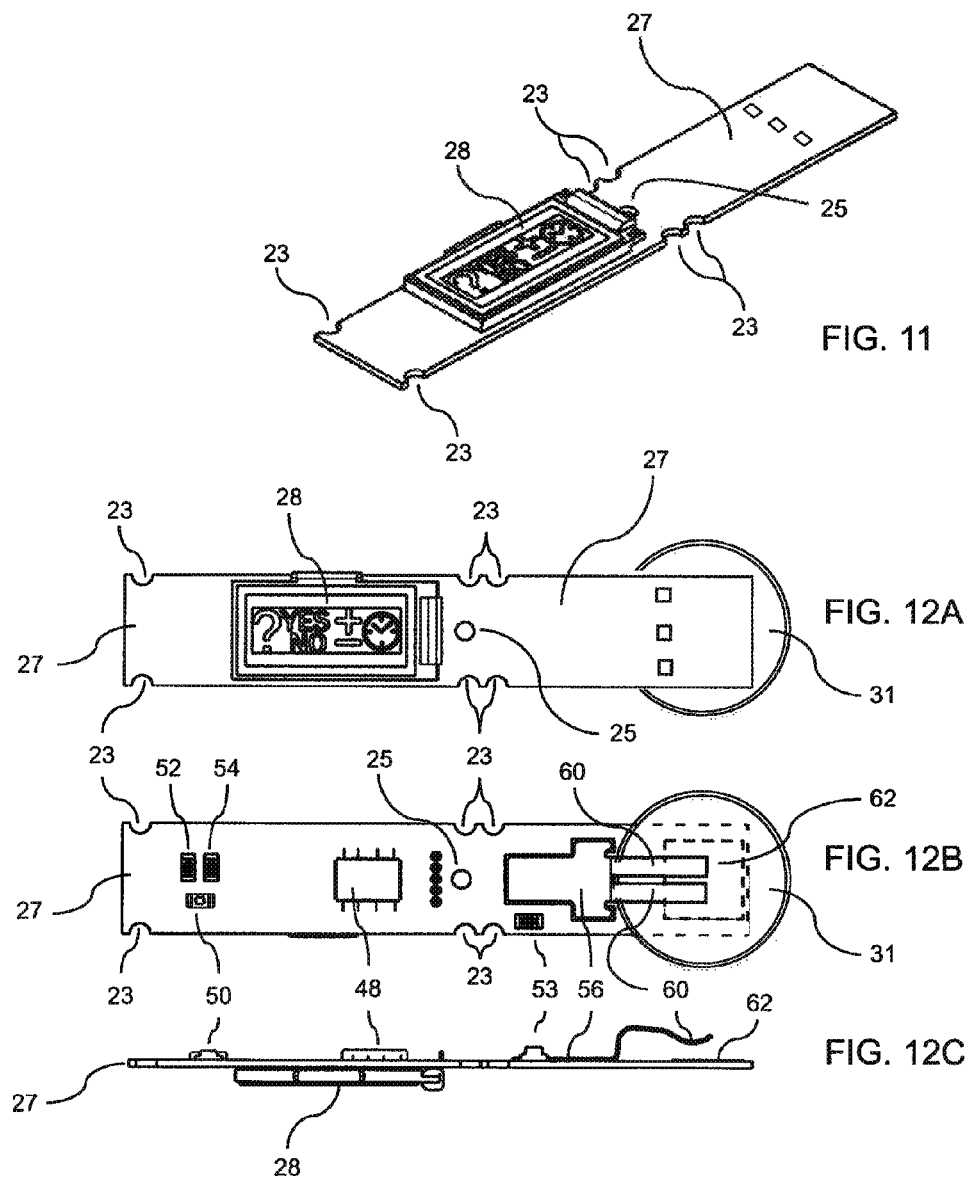

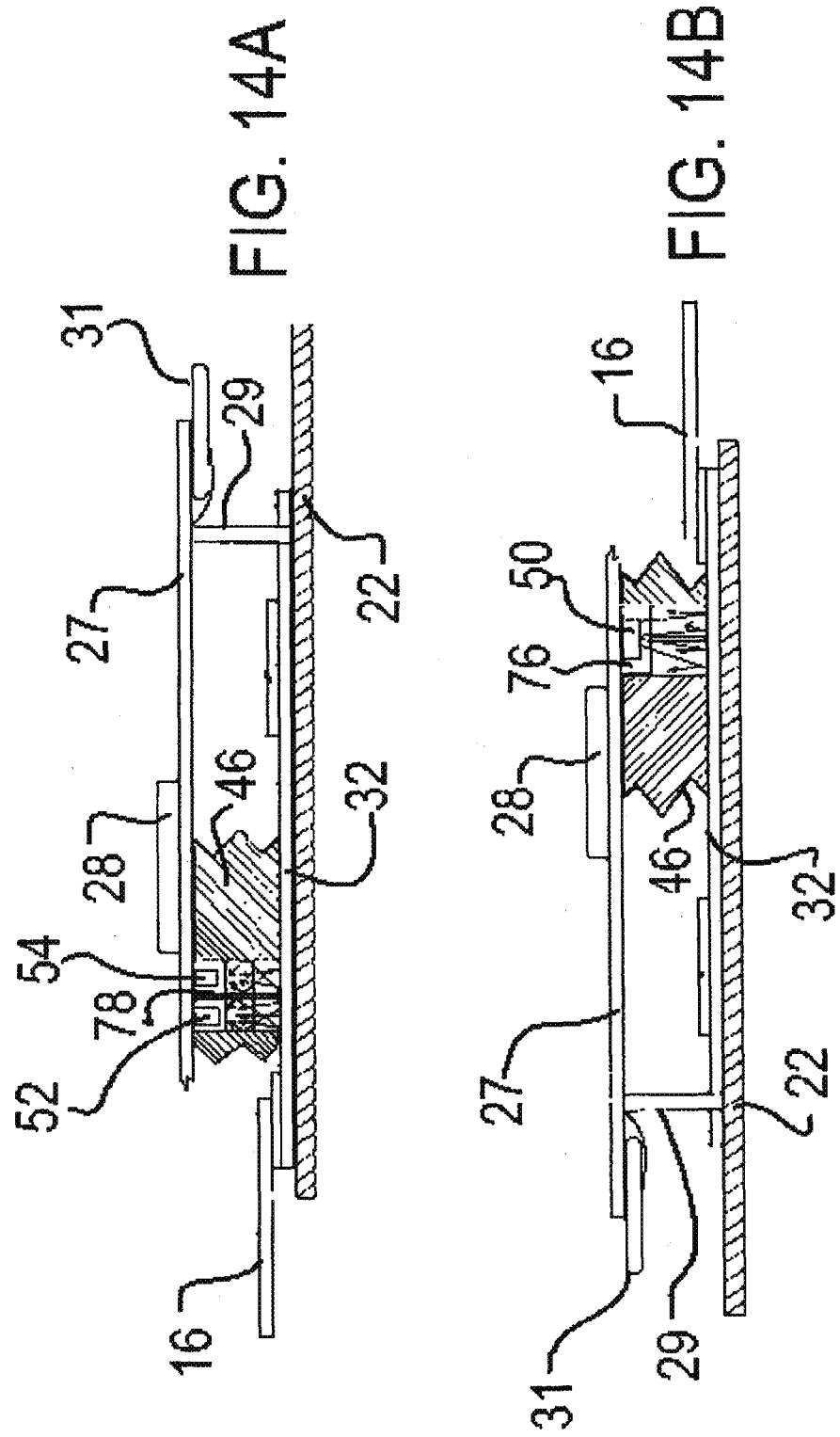

ELECTRONIC ANALYTE ASSAYING DEVICE

CLAIM OF PRIORITY

This application is a continuation divisional application of U.S. application Ser. No. 12/967,971, filed on Dec. 14, 2010 entitled IMPROVED ELECTRONIC ANALYTE ASSAYING DEVICE, which claims priority to Provisional Application Ser. No. 61/389,050, filed on Oct. 1, 2010, the contents of which are incorporated in their entirety herein by reference.

FIELD OF THE INVENTION

The invention relates to diagnostic assays for analytes in a liquid sample. In particular, the invention relates to an improved electronic device for detecting an analyte in a body fluid and a method of using the device for assay test results.

BACKGROUND OF THE INVENTION

Many types of ligand-receptor assays have been used to detect the presence of various substances in body fluids, such as urine, saliva, or blood. Many of these assays are designed to make a quantitative determination, but in many circumstances all that is required is a qualitative positive/negative indication. Examples of such qualitative assays include blood typing, pregnancy testing, and many types of urinalysis. For these tests, visually observable indicia, such as the presence of agglutination or a color change, are preferred.

Qualitative 'positive/negative' assays require a high degree of sensitivity due to the often low concentration of the ligand of interest present in the test fluid. False positives can be troublesome, particularly with agglutination and other rapid detection methods such as dipstick and color change tests. Because of these problems, sandwich assays and other sensitive detection methods which use metal sols or other types of colored particles have been developed.

A common type of device that incorporates the use of such biological interactions is a test strip assay device, U.S. Pat. No. 6,485,982, which is incorporated herein by reference in its entirety, describes a diagnostic device formed of an elongate outer casing which houses an interior permeable material (such as fiber glass) capable of transporting an aqueous solution by capillary action, wicking, or simple wetting. The casing defines a sample inlet, and interior regions, which are designated as a test volume and a reservoir volume. The reservoir volume is disposed in a section of the test cell spaced apart from the inlet and is filled with sorbent material. The reservoir acts to receive liquid transported along a flow path defined by the permeable material and extending from the inlet and through the test volume. In the test volume is a test site comprising a first protein having a binding site specific to a first epitope of the ligand immobilized in fluid communication with the flow path (e.g., bound to the permeable material or to latex particles entrapped in or bonded to the permeable material). A window, such as a hole or transparent section of the casing, permits observations of the test site through the casing wall. The method of use of the test cell requires the use of a conjugate comprising a second protein bound to colored particles, such as a metal sol or colloid, preferably gold. U.S. Pat. No. 7,045,342, which is incorporated herein by reference in its entirety, describes an improved diagnostic device including a test strip comprising of a biphasic chromatographic medium. The biphasic chromatographic medium is formed of a release medium joined to a capture medium located downstream of the release medium. The release and capture media preferably comprise two different materials, or phases, having different specific characteristics. The two phases are joined together to form a single liquid path such that a solvent front can travel unimpeded from the proximal (upstream) end of the release medium to the distal (downstream) end of the capture medium.

A purely visual (i.e., human eye dependent) diagnostic test as exemplified above requires proper interpretation of the results. However, devices have been developed to provide an automated detector system for determining sufficient color development at a test site and for also ensuring that the color intensity is read/interpreted at the appropriate time after sample application. For example, U.S. Pat. No. 5,837,546 discloses an integrated reader and a test-strip wherein the test strip is provided with additional electrodes which sense the presence of fluid on the test strip which generates a signal to switch on the sensing electronics. The device includes a housing having an exterior surface and defining an interior area. A sample receptor receives the sample. Reagents on a test strip react with the sample to yield a physically detectable change which correlates with the amount of selected analyte in the sample. A detector responds to the physically detectable change and produces an electrical signal which correlates to the amount of the selected analyte in the sample. A processor converts the electrical signal to a digital output. In another example, U.S. Pat. No. 7,220,597 discloses an integrated reader with a test-strip activated by a mechanical switch means, wherein the switch means is responsive to the removal of a lid from the device housing. The device also requires a sample sensor for detecting the presence of the sample, wherein sample presence signal generates a time delay, and a reaction sensor responsive to the time delay for detecting an analyte in the fluid sample.

Although diagnostic devices, such as those described above, show improvements over the art, there still remains a need for test devices providing greater accuracy and sensitivity. For example, in the field of pregnancy testing, accurate and rapid detection of low levels of hCG is desired to allow consumers to confirm pregnancy soon after conception has occurred.

SUMMARY OF THE INVENTION

The present invention recognizes and addresses disadvantages of prior art constructions and methods. Various combinations and sub-combinations of the disclosed elements, as well as methods of utilizing same, which are discussed in detail below, provide other objects, features, and aspects of the present invention.

In one preferred embodiment of the present invention, a diagnostic device for detecting the presence of an analyte in a fluid sample comprises a casing having a display, a test strip mounted in the casing, a processor mounted in the casing, and a first sensor mounted in the casing and operatively coupled to the processor. The processor is configured to receive a signal from the first sensor when the device is exposed to ambient light thereby causing the device to become activated.

In some embodiments, when the device is activated, the device performs a self-diagnostic test to ensure that the device is operating within pre-established parameters.

In other embodiments, the device further comprises a light source mounted in the casing and operatively coupled to the processor, the light source configured to illuminate a portion of the test strip. In some of these embodiments, a second sensor is mounted in the casing and is operatively coupled to the processor, the second sensor being positioned to sense an area corresponding to a test result site on the test strip. In still other of these embodiments, a third sensor is mounted in the casing and operatively coupled to the processor, the third sensor being positioned to sense an area adjacent to the test result site on the test strip. In yet other of these embodiments, the processor is configured to receive a signal from the second and third sensor, and perform a comparison of the second sensor signal reading with the third sensor signal reading. The comparison further comprising calculating a difference value by subtracting one of the second sensor signal reading and the third sensor signal reading from the other of the second sensor signal reading and the third sensor signal reading.

In yet other embodiments, the processor is configured to confirm the detection of a valid fluid front when the difference value exceeds a predetermined valid fluid front threshold value. In still other embodiments, the processor is configured to display a positive test result message on the display if the difference value is greater than an early result threshold value at any time after a predetermined time period from the detection of a valid fluid front. In some of these embodiments, the predetermined time period is less than a standard time period. In one of these embodiments, the predetermined time period is approximately 90 seconds.

In still other preferred embodiments, the processor is configured to display at a predetermined time period from the detection of a valid fluid front a positive test result message on the display if the difference value exceeds a predetermined threshold value and a negative test result message on the display if the difference value is less than the predetermined threshold value. In still other embodiments, the predetermined time period is approximately 3 minutes.

In some preferred embodiments, a light shield is mounted in the casing, wherein the light shield is configured to apply pressure across a width of the test strip to prevent channeling of fluid flow along a length of the test strip. In some of these embodiments, the light shield further comprises a first through hole configured to direct light from the light source onto a portion of the test strip, and a second through hole configured to direct reflected light from the portion of the test strip to the second sensor and the third sensor.

In still other embodiments, a sample receiving member is coupled to the test strip at a first end for receiving a fluid sample on the test strip. In other embodiments, the light source is a light emitting diode, and the first and the second sensors are photo sensors.

In one preferred method for detecting the presence of an analyte in a fluid sample, the method comprising the steps of providing a diagnostic device comprising a casing having a display, a test strip mounted in the casing, a processor mounted in the casing, and a first sensor mounted in the casing and operatively coupled to the processor, the sensor being configured to provide a signal to the processor when the first sensor detects ambient light. The method also comprises the step of covering the diagnostic device so as to prevent the first sensor from sensing ambient light thereby preventing the diagnostic device from activating.

In some embodiments, the method further comprises the step of activating the device when the cover is removed and the first sensor is exposed to ambient light. In some of these embodiments, the method further comprises the step of performing a diagnostic self-test after the step of activating to ensure the device is operating within pre-established parameters.

In some embodiments, the step of covering comprises of covering a light port on the casing of the device for directing ambient light to the first sensor. In some embodiments, the step of covering further comprises sealing the diagnostic device in a light impervious material. In some of these embodiments, the light impervious material is a foil wrapper.

In still other embodiments, the method further comprises the steps of providing a light source mounted in the casing that is operatively coupled to the processor, wherein the light source is configured to illuminate a portion of the test strip, providing a second sensor mounted in the casing and operatively coupled to the processor wherein the second sensor is positioned proximate the test strip so as to sense an area corresponding to a test result site, providing a third sensor mounted in the casing and that is operatively coupled to the processor, wherein the third sensor is positioned proximate the test strip so as to sense an area adjacent to the test result site, illuminating the test strip with the light source, receiving a signal by the processor from the second and third sensors, and performing a comparison of the second sensor signal reading with the third sensor signal reading, wherein the comparison further comprises calculating a difference value by subtracting the signal readings from the sensors.

In some of these embodiments, the method further comprises the step of displaying a positive test result message on the display when the signal reading is greater than an early result threshold value at any time after a predetermined time period. In yet other of these embodiments, the early result threshold value is greater than a normal predetermined threshold value and the time period is less than a standard time period.

In still other embodiments, the method further comprises the step of minimizing the effect of fluid channeling along the length of the test strip by providing pressure across the width of the test strip. In some of these embodiments, the pressure across the width of the test strip is provided by a light shield placed in contact with the test strip.

In another preferred embodiment of a diagnostic device for detecting the presence of an analyte in a fluid sample, the device comprises a casing having a display, a test strip mounted in the casing, the test strip having a length and a width and a test result site located thereon, a light shield mounted in the casing adjacent the test strip, the light shield having at least two through holes formed therein, a processor mounted in the casing, a sensor mounted in the casing adjacent one of the at least two through holes, the sensor being operatively coupled to the processor, and a light source mounted in the casing adjacent to the other of the at least two through holes, the light source being operatively coupled to the processor. A portion of the light shield is configured to exert pressure across the width of the test strip to prevent fluid channeling along the length of the test strip.

In some embodiments, a second sensor is mounted in the casing adjacent to one of the at least two through holes, the second sensor being operatively coupled to the processor, wherein the derivative is calculated by subtracting a signal from one of the sensor and the second sensor from a signal of the other of the sensor and the second sensor. In some of these embodiments, the processor is configured to receive a signal from each of the sensors, and when a derivative of the signals is greater than an early positive result threshold value at any time after a predetermined time period, the processor is configured to display a positive result message on the display. In other of these embodiments, the early positive result threshold value is greater than a normal predetermined threshold value and the predetermined time period is less than a standard time period.

In still another preferred embodiment, a diagnostic device for detecting the presence of an analyte in a fluid sample, the device comprises a casing having a display, a test strip mounted in the casing, the test strip having a test result site located thereon, a light shield mounted in the casing adjacent the test strip, the light shield having at least two through holes formed therein, a processor mounted in the casing, a sensor mounted in the casing adjacent one of the at least two through holes, the sensor being operatively coupled to the processor and a light source mounted in the casing adjacent to the other of the at least two through holes, the light source being operatively coupled to the processor. In this embodiment, the processor is configured to receive a signal from the sensor indicative of a reading of the test strip test result site, and when the reading is greater than an early positive result threshold value at any time after a predetermined time period, the processor is configured to display a positive result on the display.

In some embodiments, the early positive result threshold value is greater than a normal predetermined threshold value and the predetermined time period is less than a standard time period. In other of these embodiments, the predetermined time period is approximately 90 seconds. In still other embodiments, the standard time period is approximately 3 minutes.

Various combinations and sub-combinations of the disclosed elements, as well as methods of utilizing same, which are discussed in detail below, provide other objects, features, and aspects of the present invention.

The accompanying drawings, which are incorporated in and constitute a part of this specification, illustrate one or more embodiments of stacked displays of the present invention.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings, in which:

FIGS. 1 and 2 are perspective views of the top and left side of the device with the cap and with the cap removed, respectively, in accordance with one embodiment of the present invention;

FIGS. 3 and 4 are respective top and bottom plan views of the device of FIGS. 1 and 2;

FIGS. 5 and 6 are respective back and front plan views of the device of FIGS. 1 and 2;

FIGS. 7 and 8 are respective left side and right side plan views of the device of FIGS. 1 and 2;

FIG. 11 is a perspective view of the top and left side of the printed circuit board and display for use in the device of FIGS. 1-8;

FIGS. 12A and 12B are respective top and bottom views of the printed circuit board of FIG. 11 with battery;

FIG. 12C is a side view of the printed circuit board of FIG. 11;

FIG. 14A is a partial left side sectional view of the device of FIG. 9B;

FIG. 14B is a partial right side sectional view of the device of FIG. 9B;

Figure 9A:
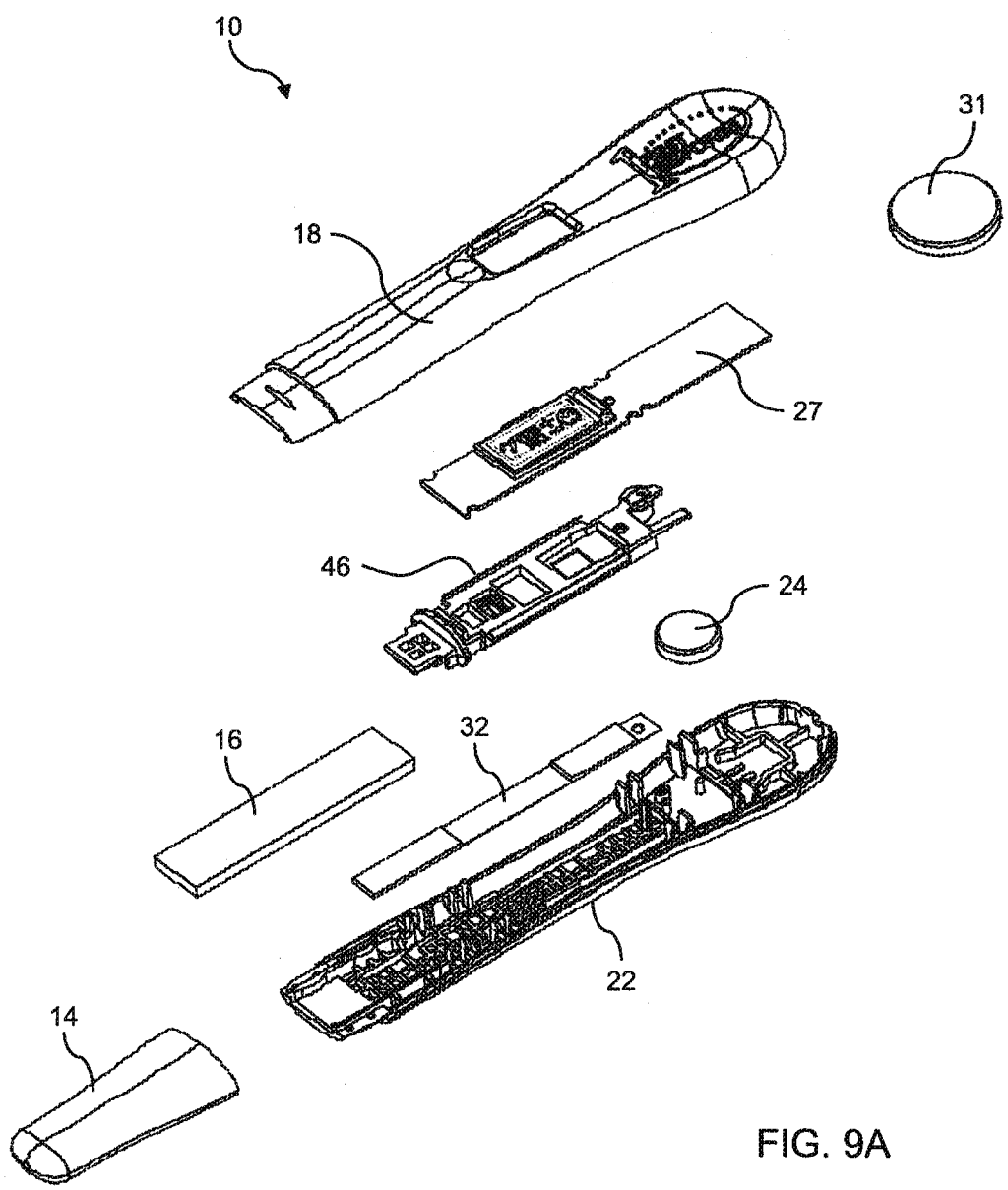
FIG. 9A is an exploded assembly view of the device of FIGS. 1-8.

Repeat use of reference characters in the present specification and drawings is intended to represent same or analogous features or elements of the invention according to the disclosure.

DETAILED DESCRIPTION OF THE PREFERRED EMBODIMENT

Reference will now be made in detail to presently preferred embodiments of the invention, one or more examples of which are illustrated in the accompanying drawings. Each example is provided by way of explanation, not limitation, of the invention. It is to be understood by one of ordinary skill in the art that the present discussion is a description of exemplary embodiments only, and is not intended as limiting the broader aspects of the present invention, which broader aspects are embodied in the exemplary constructions. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents.

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. As used in the specification, the singular forms "a," "an," "the," include plural referents unless the context clearly dictates otherwise.

The invention comprises of an electronic device for conducting an immunoassay and a method of using the device. The inventive device is characterized in that it provides an opto-electronic processing means in an improved single-step device that increases the efficiency and effectiveness of a simplified test that untrained personnel can use to reliably assay a liquid sample for the presence of extremely small quantities of a particular ligand with high degree of accuracy. The invention is ideal for use in over-the-counter (OTC) diagnostic test kits which will enable a consumer to self diagnose, for example, pregnancy, ovulation, sexually transmitted infections, and other bacterial infections or clinical abnormalities which result in the presence of an antigenic marker substance in a body fluid, including determination of the presence of drugs and their metabolites or toxins. The assay process and the test device are engineered specifically to detect the presence of a pre-selected individual ligand present in body fluids or other fluids.

The term "body fluid," as used herein, refers to a sample of biological origin, or a sample derived from the sample of biological origin. The biological samples include, but are not limited to, blood, plasma, serum, saliva, cerebral spinal fluid, pleural fluid, milk, lymph, sputum, semen, urine, stool, tear, saliva, needle aspirate, external section of the skin, respiratory, intestinal, or genitourinary tract, tumor, organ, cell culture, cell culture constituent, tissue sample, tissue section, whole cell, cell constituent, cytospin, or cell smear.

The inventive device can be used to detect any analyte which has heretofore been assayed using known immunoassay procedures, or known to be detectable by such procedures, using polyclonal or monoclonal antibodies or other proteins comprising binding sites for ligands. Various specific assay protocols, reagents, and proteins can be used according to the present invention such as, for example, those described in U.S. Pat. No. 4,313,734, which is incorporated herein by reference.

As used herein, an "analyte" refers to the material to be detected by use of the device and method of the present invention. "Analyte" includes but is not limited to: antigens, antibodies, hormones (such as FSH, TSH, hCG, LH), drugs, proteins associated with a cell ("cell proteins"), secreted proteins, enzymes, cell surface or transmembrane proteins, glycoproteins and other proteins, peptides, and carbohydrates.

As used herein, "antibody" refers to a polypeptide substantially encoded by an immunoglobulin gene or immunoglobulin genes, or fragments thereof, which recognizes and binds an antigen. The recognized immunoglobulin genes include the kappa, lambda, alpha, gamma, delta, epsilon, and mu constant region genes, as well as the immunoglobulin variable region genes. Antibodies include fragments, such as Fab', F(ab)2, Fabc, and Fv fragments. The term "antibody," as used herein, also includes antibody fragments either produced by the modification of whole antibodies or those synthesized de novo using recombinant DNA methodologies, and further include "humanized" antibodies made by now conventional techniques.

As used herein, a "capture antibody" should be understood as an antibody, such as a monoclonal or polyclonal antibody, attached directly or indirectly to a substrate, such as a solid phase. The capture antibody can include at least one binding member that recognizes and binds a particular, distinct epitope of an antigen, such as hCG. Embodiments of the present invention preferably also make use of a conjugate (labeled binding member) comprising an antibody bound to a detectable label component (which can be colored particles, such as a metal sol or colloid, preferably gold).

The diagnostic device of the invention preferably makes use of a conjugate comprising a protein bound to a label component. Any detectable label recognized in the art as being useful in various assays could be used in the present invention. In particular, the detectable label component can include compositions detectable by spectroscopic, photochemical, biochemical, immunochemical, or chemical means. The label component thus produces a detectable signal. Exemplary labels include fluorescent dyes, chemiluminescent compounds, radioisotopes, electron-dense reagents, enzymes, or colored particles (such as a metal sol or colloid, preferably gold). The label component can generate a measurable signal, such as radioactivity, fluorescent light, color, or enzyme activity, which can be used to identify and quantify the amount of label bound to a test site. Thus, the label component can also represent the presence of a particular antigen bound thereto.

The assay can take two distinct forms, depending on whether the assay is designed to exploit the "sandwich" or "competitive" technique. In embodiments wherein the device of the invention makes use of a sandwich technique, the antibody used in the detection comprises a binding region or site which binds to an epitope on the analyte for detection, such as hCG. The antibody designated as label antibody preferably has a label component bound thereto to form a labeled conjugate (labeled binding member), which reacts with the analyte of interest to form a complex in the liquid sample. The analyte bound to the conjugate (labeled binding member) reacts with a second antibody designated as capture antibody to form a "sandwich" of the capture antibody, analyte, and conjugate antibody (labeled binding member). In certain embodiments, a biotinylated capture antibody can also be utilized. For example, the biotinylated capture antibody can include a region or site that binds to a second epitope on the analyte. In these embodiments, the resulting "sandwich" comprises a complex of the labeled conjugate {labeled binding member}—analyte—{biotinylated capture antibody}. In general, the "sandwich" complex is progressively produced as the biological sample with the analyte therein continuously moves along the test strip of the device. As more and more "sandwich" complexes are immobilized at the capture site (test site) comprising of a binding member with affinity to the biotinylated capture antibody, the label components aggregate and are detected using an electronic sensor, indicating the presence of a particular analyte in the biological sample. The electronic sensor may be photo-optic or it can be other types and kinds of sensors, including magnetic sensors. When magnetic sensors are used, then magnetic particles are employed on the test strip.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Referring to FIGS. 1-8, a schematic illustration of an embodiment of device 10 is shown constructed in accordance with one embodiment of the present invention. Device 10 comprises of a molded top casing 18 and a bottom casing 22, which collectively define a hollow, elongate enclosure. A removable cap 14 is secured to one end of the casing enclosure over a sample receiving member 16. Sample receiving member 16 is positioned so that part of the sample receiving member is received in the casing enclosure and part of the sample receiving member extends from the end of the casing enclosure.

The top casing (FIGS. 1-3) is configured to provide a recessed portion 20 shaped to permit users to place their thumb into the recessed portion and their forefinger on bottom casing 22 (FIG. 4) to securely hold device 10. A raised central section (FIGS. 1-3) of top casing 18 defines a centrally located window 26 to permit a user to observe test results provided on an underlying display 28 (e.g. LCD).

Referring to FIG. 5, a battery removal tab 30 is formed therein to allow the user to open the device to properly dispose of the battery therein.

It should be understood that the above description of a device is for illustrative purposes, and other devices may be used.

Figure 9B:
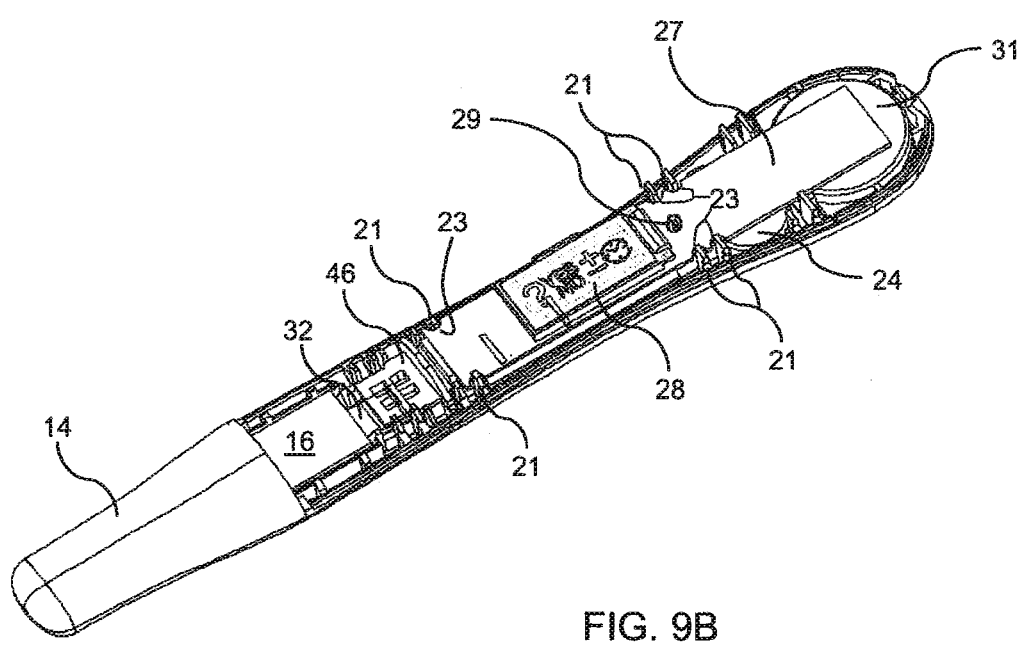
FIG. 9B is a perspective view of the top and left side of the device of FIGS. 1-8 with the top half of the casing removed.

Referring to FIG. 9A, the device is shown having a bottom case 22, a top case 18, a sample receiving member 16, a test strip 32, a light shield 46, a printed circuit board 27, a battery 31 and a desiccant 24. Referring to FIG. 9B, sample receiving member 16 and test strip 32 are received in bottom casing 22. Sample receiving member 16, in addition to providing a means for receiving the sample also serves as a filter which can remove from test samples particulate matter and interfering factors. The sample receiving member is preferentially disposed within the casing enclosure and extends to the exterior thereof. In one preferred embodiment, sample receiving member 16 preferably is a bibulous hydrophilic material which facilitates absorption and transport of a fluid sample to test strip 32. As taught in U.S. Pat. No. 6,277,650, such materials may include cellulose acetate, hydrophilic polyester, and other materials having similar properties.

Figure 10A:
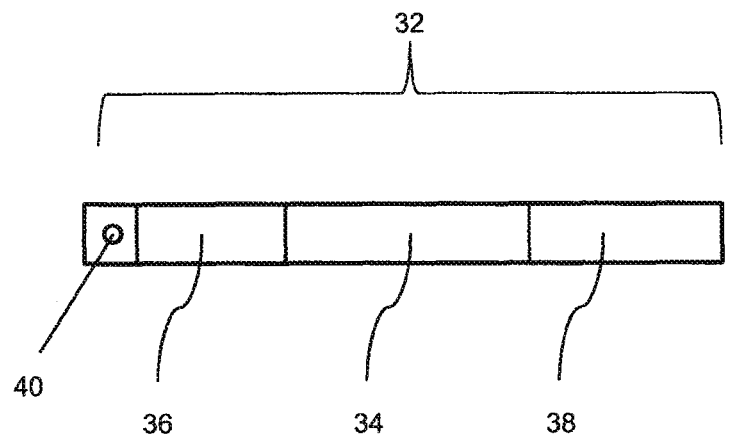
FIG. 10A is a schematic top view of a test strip according to one embodiment for use in the device of FIGS. 1-8.
Figure 13A:
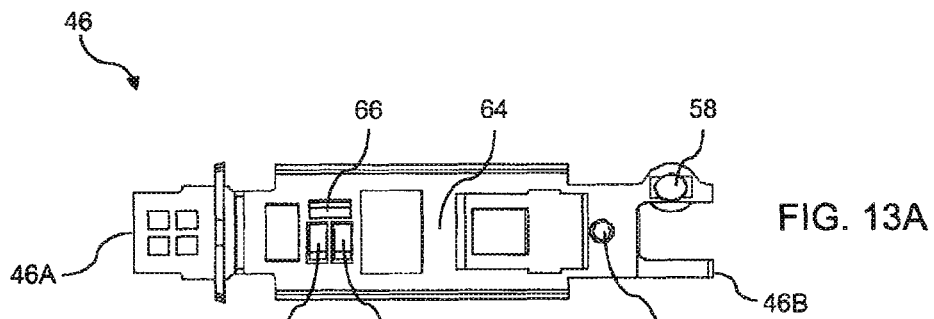
FIG. 13A is a top view of a light shield for use in the device of FIGS. 1-8.
Figure 13B:
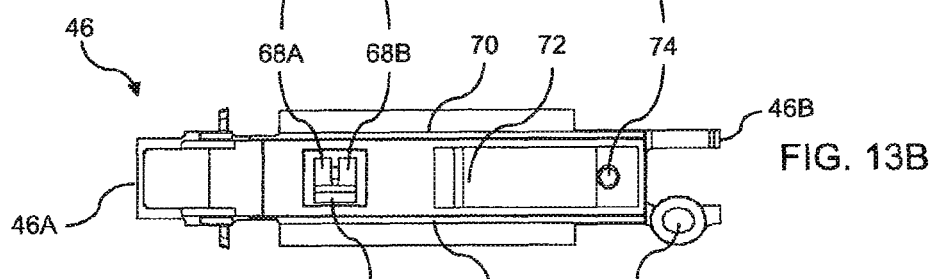
FIG. 13B is a bottom view of the light shield of FIG. 13A.
Figure 13C:
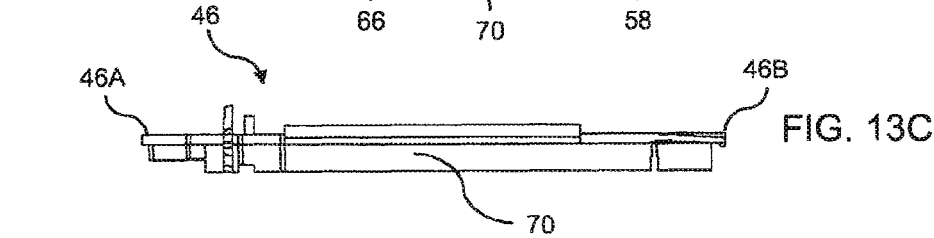
FIG. 13C is a side view of the light shield of FIG. 13A.

Various alignment structures (FIG. 9A not shown) are used to properly seat the sample receiving member 16 and test strip 32 in bottom casing 22 (FIG. 9B). Test strip 32 comprises of alignment hole 40 (FIG. 10A) formed towards the distal end of the test strip configured to receive alignment pin 29 on bottom casing 22 (FIG. 9B). Light shield 46 also comprises an alignment hole 74 (FIG. 13A) configured to receive alignment pin 29 on bottom casing 22, such that light shield 46 is position over test strip 32 (FIG. 9B). Also, a variety of alignment guides 21 maintain the light shield in correct alignment with test strip 32 and printed circuit board 27. Printed circuit board 27 has display 28 operatively connected on one side thereof. Printed circuit board 27 is maintained in alignment with the various other parts of test device 10 using alignment guides 21 and various alignment recesses 23. Mating of alignment guides 21 and alignment recesses 23 maintain proper positioning of the printed circuit board with respect to the test strip, the bottom casing and the top casing so that display 28 properly aligns with top casing window 26. A battery 31 is operatively coupled to printed circuit board 27 and provides power for all electrical parts of device 10.

Figure 10B:
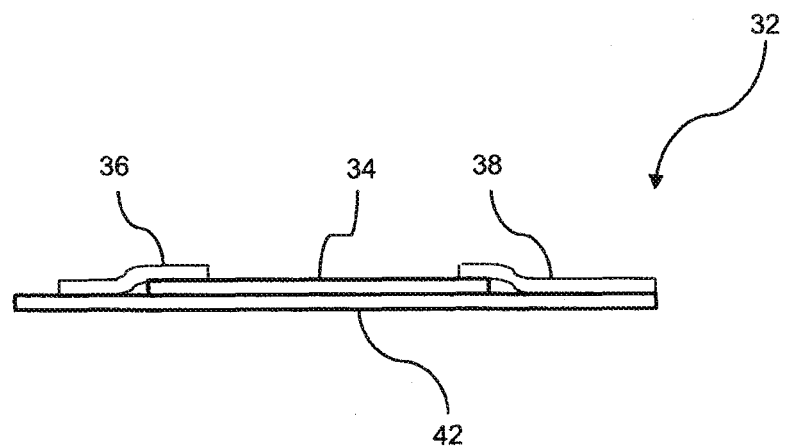
FIG. 10B is a schematic side view of the test strip of FIG. 10A.

Also, the preferred embodiment of the invention includes a test strip 32 comprising of a triphasic chromatographic medium. For ease of illustration, reference is made to FIGS. 10A and 10B. The triphasic chromatographic medium includes a release medium 38 and a reservoir pad 36 adjacent the capture medium 34. As taught in U.S. Pat. No. 6,277,650, a release medium 38 preferably comprises absorbent paper, and the capture medium 34 preferably comprises a nitrocellulose membrane. Also shown herein and as taught in the aforesaid patent, the release medium 38, the capture medium 34 and the reservoir pad 36 preferably are laminated onto an opaque plastic film or sheet 42 (FIG. 10B). Disposed upon the release medium 38 is a first binding member comprising a first monoclonal antibody reactive with a first epitope on the analyte, and labeled with a visually detectable marker, such as, colloidal gold particles, and a capture component comprising a biotinylated monoclonal antibody disposed downstream of the labeled antibody. The biotinylated antibody is reactive with a second epitope on the analyte and is capable of forming a complex with the labeled antibody and the analyte. Also disposed upon the capture medium is a site for capturing and immobilizing the complex, as previously mentioned. The capture site immobilizes thereon a capture component, preferably streptavidin, which has a high affinity for the biotin portion of the complex.

A method for manufacturing the preferred triphasic chromatographic medium is described in U.S. Pat. No. 5,846,835, the disclosure of which is incorporated herein by reference.

The preferred embodiment of test strip 32 further comprises, a reservoir pad 36 consisting of absorbent material disposed distal to, or downstream of capture medium 34 and in fluid communication therewith. The purpose of the reservoir pad 36 is to facilitate capillary action along the chromatographic substrate of test strip 32, and to absorb excess fluid sample contained with the device 10. The reservoir pad absorbent material preferably comprises absorbent paper made from cotton long linter fibers, such as identified by product codes S&S 300, S&S 470, and S&S 900 (available from Schleicher & Schuell, Inc.) or cellulosic materials, such as Whatman 3MM (available from Whatman). Referring to FIG. 10B, a side view of one embodiment of the test strip 32 is shown where the distal or downstream end of release medium 38 overlaps the proximal or upstream end of capture medium 34 and the distal or downstream end of capture medium 34 overlaps the proximal or upstream end of reservoir pad 36. Again, release medium 38 and the capture medium 34 may alternatively be connected via a butt joint rather than being in overlapping connection. These three components are laminated on a plastic backing and together form a single fluid path, and cooperate to cause sample liquid to flow along release medium 38 and the capture medium 34 into reservoir pad 36.

FIGS. 11 and 12A-12C, printed circuit board 27 is generally rectangular in shape and defines a plurality of alignment recesses 23 formed thereon. Display 28 is mounted on one side of printed circuit board 27 and is operatively coupled to a processor 48 (FIG. 12B) mounted on an opposite side of printed circuit board 27. Referring to FIG. 12B, a light source 50 is mounted on printed circuit board 27, which in one preferred embodiment is a light emitting diode (LED), but in other embodiments may be any suitable light source. In addition to light source 50, two light sensors 52 and 54 are mounted proximate to light source 50 on printed circuit board 27. Light sensors 52 and 54, in one preferred embodiment, are photo sensors. Light source 50 and photo sensors 52 and 54 are operatively coupled to processor 48. Battery 31 is received between a first terminal 56 and a second terminal 62. First terminal 56 is formed from a metal contact material and includes two identical fingers 60. First terminal 56 may be formed from any suitable conductive material and in one preferred embodiment is formed from a spring steel material. Second terminal 62 may be integrally formed on printed circuit board 27 or may be formed from a conductive material that is attached to printed circuit board 27. In either case, terminals 56 and 62 provide electrical energy from battery 31 to processor 48 and the various other electrical components on printed circuit board 27.

Still referring to FIG. 12B, a light photo sensor 53, in a preferred embodiment a photo sensor, is mounted on printed circuit board 27. Photo sensor 53 is mounted on an opposite end of processor 48 and photo sensors 52 and 54, and is configured to seat adjacent a light port 12 (FIG. 4) formed in bottom casing 22. Photo sensor 53 is operatively coupled to processor 48 such that when photo sensor 53 detects ambient light device activates and runs a self-diagnostic test to ensure that the device is operating within pre-established parameters. Thus, unlike mechanical and fluid mechanisms used to activate prior art electronic assay devices, device 10 uses photo sensor 53, which is ported to the bottom casing exterior by light port 12 to detect ambient light (as shown in FIG. 4).

In one preferred embodiment, when device 10 is manufactured, light port 12 is covered to prevent ambient light from reaching photo sensor 53 thereby preventing device 10 from activating. Preventing photo sensor 53 from sensing ambient light may be accomplished by taping over light port 12 opening or by placing device 10 into a light impervious wrapper or pouch. For purposes of the present invention, the terms "wrapper" or "pouch" should be broadly construed to mean a foil wrapper, a box, a sleeve, a tube or any other suitable receptacle or covering that is light impervious and that prevents ambient light from reaching photo sensor 53.

Once device 10 is packaged, the device is maintained in sleep mode until a user opens the wrapper thereby allowing ambient light to reach the photo sensor. Upon detecting ambient light, a signal is communicated from photo sensor 53 to processor 48, which is configured to activate test device 10 and run at least one diagnostic test and display a "clock" icon on the LCD screen. In testing several thousand devices, this method of activation has proven to be extremely reliable, with no device failures due to the activation technology. Upon device activation, display 28 shows a "clock" icon which provides the user with a visual aid to confirm that the device is ready for use.

Figure 13D:
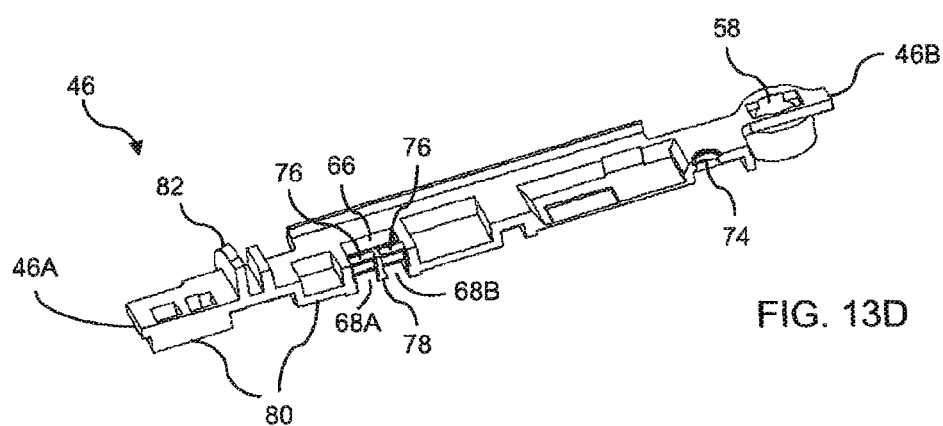
FIG. 13D is a perspective sectional view of the top and left side of the of the light shield of FIG. 13A.

Referring to FIGS. 13A-13D, light shield 46 is shown having a first end 46A and an opposite second end 46B. A top surface 64 of light shield 46 defines a first through hole 66 and two additional through holes 68A and 68B. Through holes 66 and 68A and 68B are positioned in light shield 46 so that they align with test result site on capture medium 34. Opposing rails 70 formed on a bottom surface 72 of light shield 46 assist in aligning the light shield with test strip 32. Additionally, a hole 74 is configured to receive bottom casing pin 29 (FIG. 9B) to also guide light shield 46 into proper alignment with test strip 32. The light shield 46 as shown in FIGS. 13A-13D also includes an aperture 58 which aligns with light port 21 of bottom casing 22 to direct ambient light to photo sensor 53 on printed circuit board 27. Referring in particular to FIG. 13D, first through hole 66 is separated from the additional through holes 68A and 68B by a first common wall 76. First common wall 76 begins from light shield top surface 64 and extends downward most but not all the way to light shield bottom surface 72. Again referring to FIG. 13D, a second common wall 78 separates through hole 68A from through hole 68B and extends from light shield top surface 64 to light shield bottom surface 72. First common wall 76 prevents light from light source 50 from shining directly onto photo sensors 52 and 54, while second common wall 78 prevents sensor cross-contamination or cross-talk between photo sensors 52 and 54. Light shield 46 is mounted intermediate printed circuit board 27 and bottom casing 22 (as shown in FIG. 9B). Test strip 32 is positioned intermediate light shield 46 and bottom casing 22 so that first through hole 66 aligns with light source 50 and additional through holes 68A and 68B align with photo sensors 52 and 54, respectively. Various areas 80 of light shield 46 are configured to exert pressure across a width of test strip 32. Lateral pressure across test strip 32 helps to prevent channeling of fluid flow along the length of test strip 32. To assist in maintaining pressure exerted by light shield 46 on test strip 32, a flange 82 may be formed on light shield top surface 64, which is configured to engage top casing 18 when top casing 18 and bottom casing 22 are attached to one another.

Referring to FIGS. 14A and 14B, the relative position of light shield 46 and test strip 32 is shown. Referring in particular to FIG. 14A, bottom casing alignment pin 29 engages test strip 32, light shield 46 (not shown in FIGURE due to partial cutaway view) and printed circuit board 27 to maintain the longitudinal positioning of these components with respect to one another and bottom casing 22. The longitudinal positioning maintains through holes 68A and 68B (FIG. 13D) in alignment with respective photo sensors 52 and 54 on the printed circuit board. That is, sensor 52 aligns with through hole 68A and test result site, and sensor 54 aligns with through hole 68B and area adjacent the test result site. Referring particularly to FIG. 14B, light shield through hole 66 aligns with light source 50 on printed circuit board 27. In the preferred embodiment, light source 50 is a light emitting diode (LED) and is configured to illuminate both test result site and area adjacent the test result site. Use of an LED provides a very strong light source that acts to normalize the effect of ambient light that may penetrate from outside the housing. If the LED light source is not adequately controlled, outside ambient light can interfere with the interior LED light and affect the test result. Moreover, use of a single LED also eliminates the possibility of intensity variability that occurs in multiple LED systems.

First common wall 76, positioned intermediate through holes 68A and 68B and through hole 66, prevents light from light source 50 from shining directly onto photo sensors 52 and 54. Moreover, second common walls 78 prevents light from test result site from reflecting onto photo sensor 54 and conversely light from area adjacent the test result site from reflecting onto photo sensor 52. In this way, there is no cross contamination of reflected light from the test result site and the area adjacent the test result site on the photo sensors.

As previously stated, light sensors 52 and 54 are photo sensors that target respectively test result site and area adjacent the test result site. Area adjacent the test result site is used to establish a background measurement for use in determining the level of analyte present in the fluid sample. Use of dual photo sensors provides more accurate measurement of the target areas to better evaluate test line color and migration of the labeled binding member for determining the validity of a test result. Effectiveness of the differentiation between test result site and area adjacent the test result site is optimized to improve accuracy through enhancement of both the distance between photo sensors 52 and 54 and the position of light source 50 with respect to the photo sensors.

Figure 15:
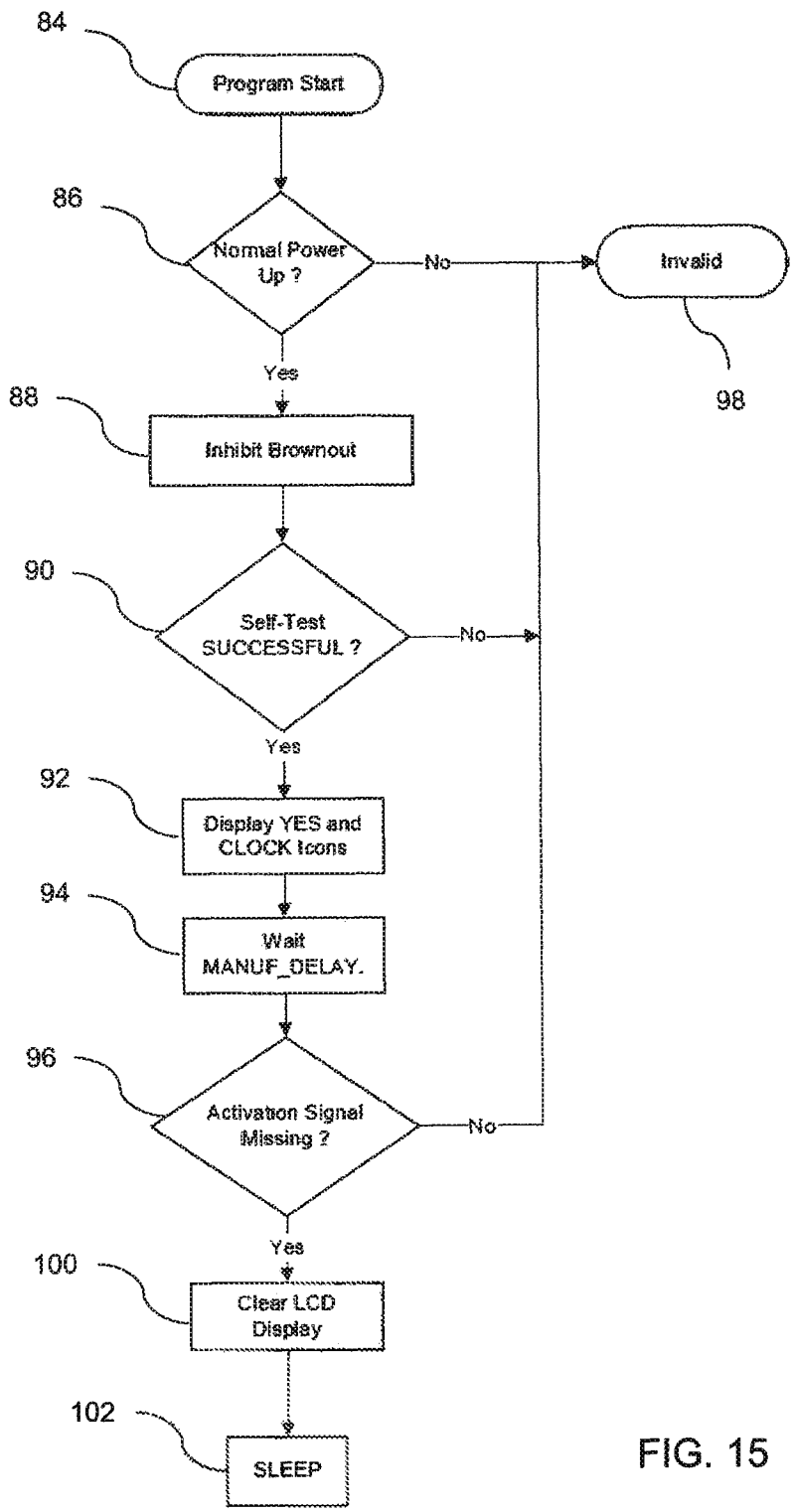
FIG. 15 illustrates a flow process carried out by the device of FIGS. 1-8 during assembly.

Referring to FIG. 14B, light is emitted from light source 50 directly onto both test result site and area adjacent the test result site. Referring to FIG. 14A, the projected light from light source 50 reflects off of the test result site and area adjacent the test result site on capture medium 34, and is directed via the respective walls of the through holes onto photo sensors 52 and 54 sensors. Each photo sensor generates an electrical signal based on the magnitude of the reflected light received by the photo sensor. The electrical signals are operatively communicated to processor 48 where the signals are digitized and computed by the processor. The signals received from photo sensors are representative of the amount of labeled binding member captured at test result site, and of a background reading from the area adjacent the test result site, In one preferred embodiment, the computation comprises the step of subtracting a value representative of the test result site signal from a value representative of the adjacent area signal. The processor than compares the resultant value to predetermined threshold values stored in memory in a lookup table to determine whether one of a plurality of test results has been met. Referring to FIG. 15, the flow process carried out by the processor 48 during assembly of the device is shown. At step 84, processor 48 runs a program consisting of initializing memory, registers, and I/O ports. The processor then checks, at step 86, whether the device powered up normally. If not, at step 98, the device displays an invalid message. If power up was normal, then at step 88 the processor inhibits brownout and a self-test is carried out, at step 90. If the self-test was unsuccessful, then at step 98 the device displays an invalid message. Otherwise, at step 92, display 28 displays "YES+" and "clock" icons. Processor 48 then waits for a predetermined time period, which in one embodiment is 24 hours, to determine and confirm that no activation signal (e.g. ambient light) is present, at step 96. If an activation signal is present, then at step 98 the device displays an invalid message. Otherwise in the absence of an activation signal display 28 is cleared, at step 100, and the device enters a deactivated (Sleep) mode at step 102.

Figure 16:
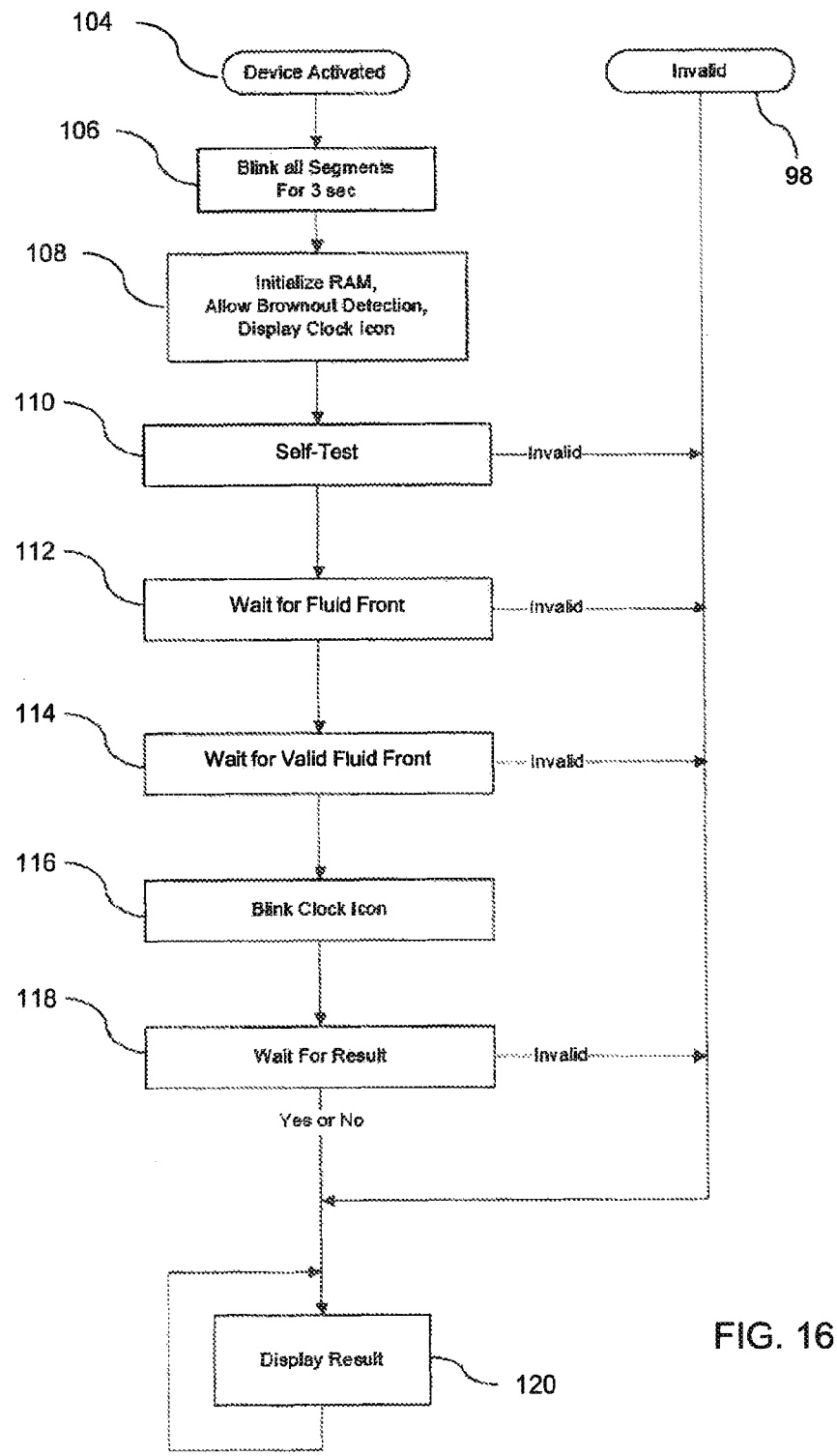
FIG. 16 illustrates a flow process carried out by the device of FIGS. 1-8 while the device is waiting for receipt of a fluid sample.

Referring to FIG. 16, device 10 is activated at step 104 once the wrapper, covering or packaging of the device has been opened and ambient light is detected by photo sensor 53. At step 106, the processor causes all icons to blink for a brief period on display 28. Afterwards at step 108, RAM memory is initialized, brownout (low voltage condition) detection is carried out, and the "clock" icon is displayed. At step 110, a self-test is performed. If errors are detected, an invalid message is displayed at step 98. Otherwise, at step 112, the system waits for detection of a fluid front on test strip 32. Following the detection of the fluid front at step 114, the system monitors the migration of the labeled binding member to determine that a valid fluid front is present. If not, then at step 98 the device displays an invalid message. If, on the other hand, a valid fluid front is detected, the "clock" icon blinks on display 28 as the device waits for the test results at step 118. Once results are determined at step 118, the results are displayed at step 120.

Figure 17A:
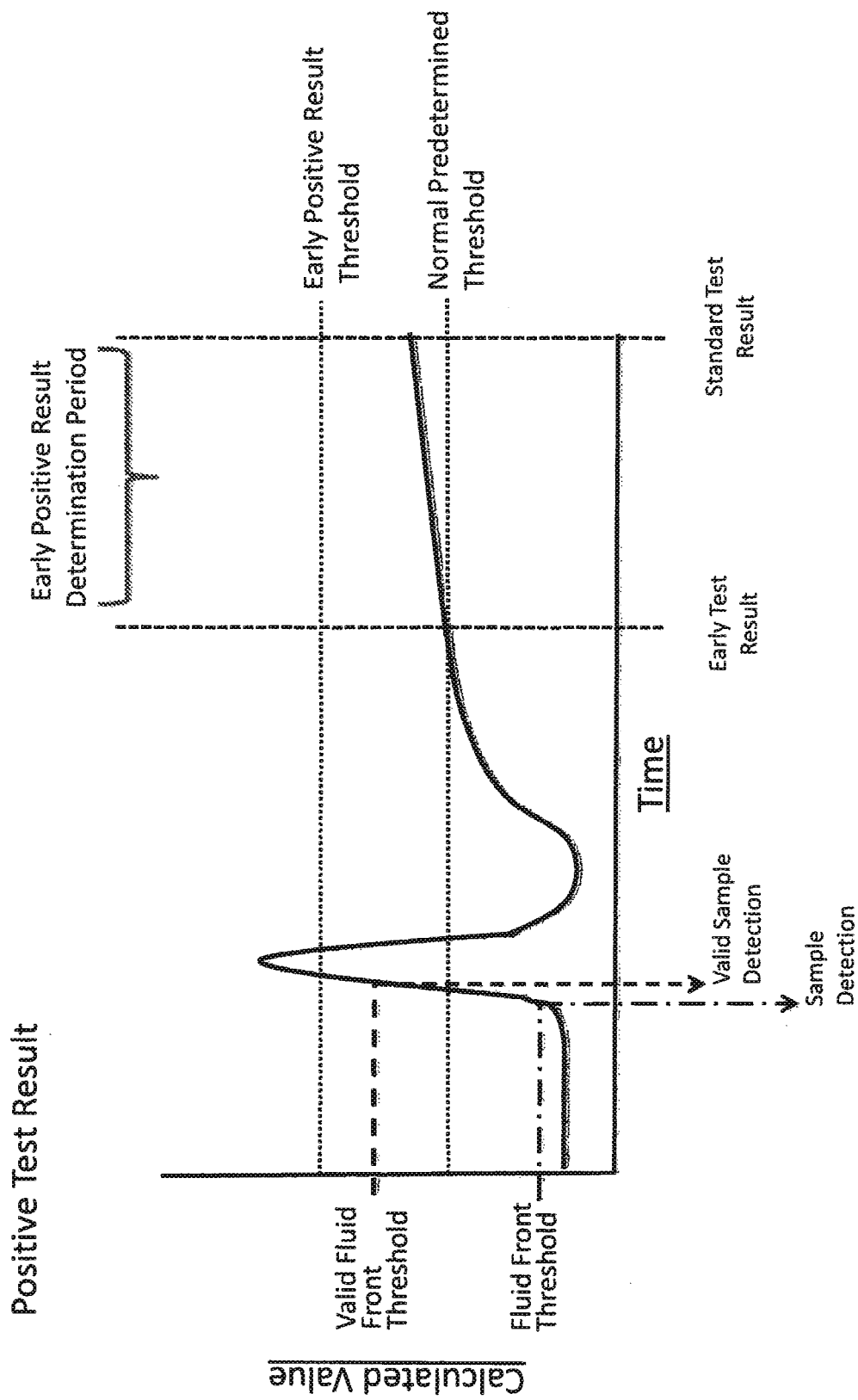
FIGS. 17A-C are graphical illustration of test results.
Figure 17B:
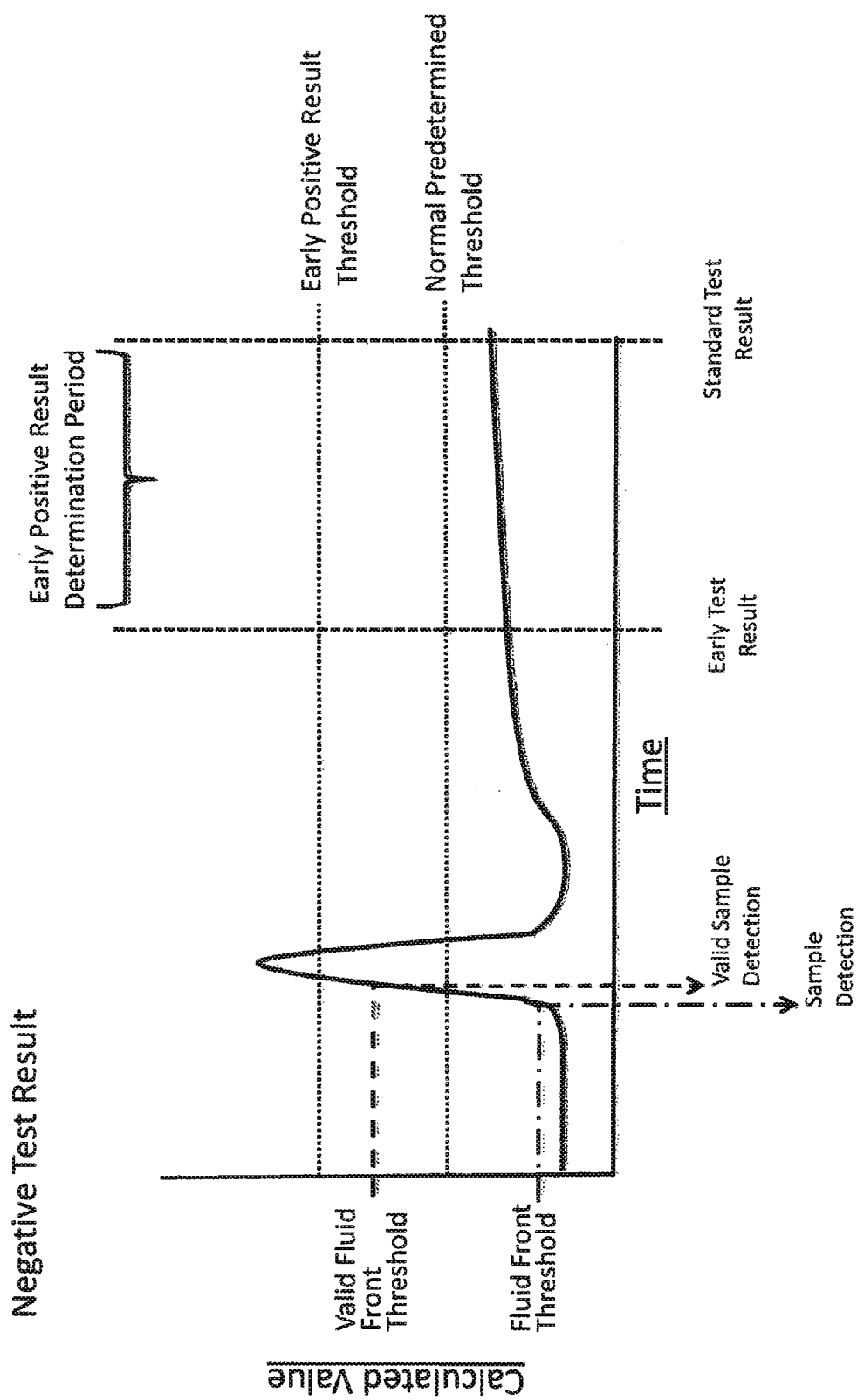
Figure 17C:
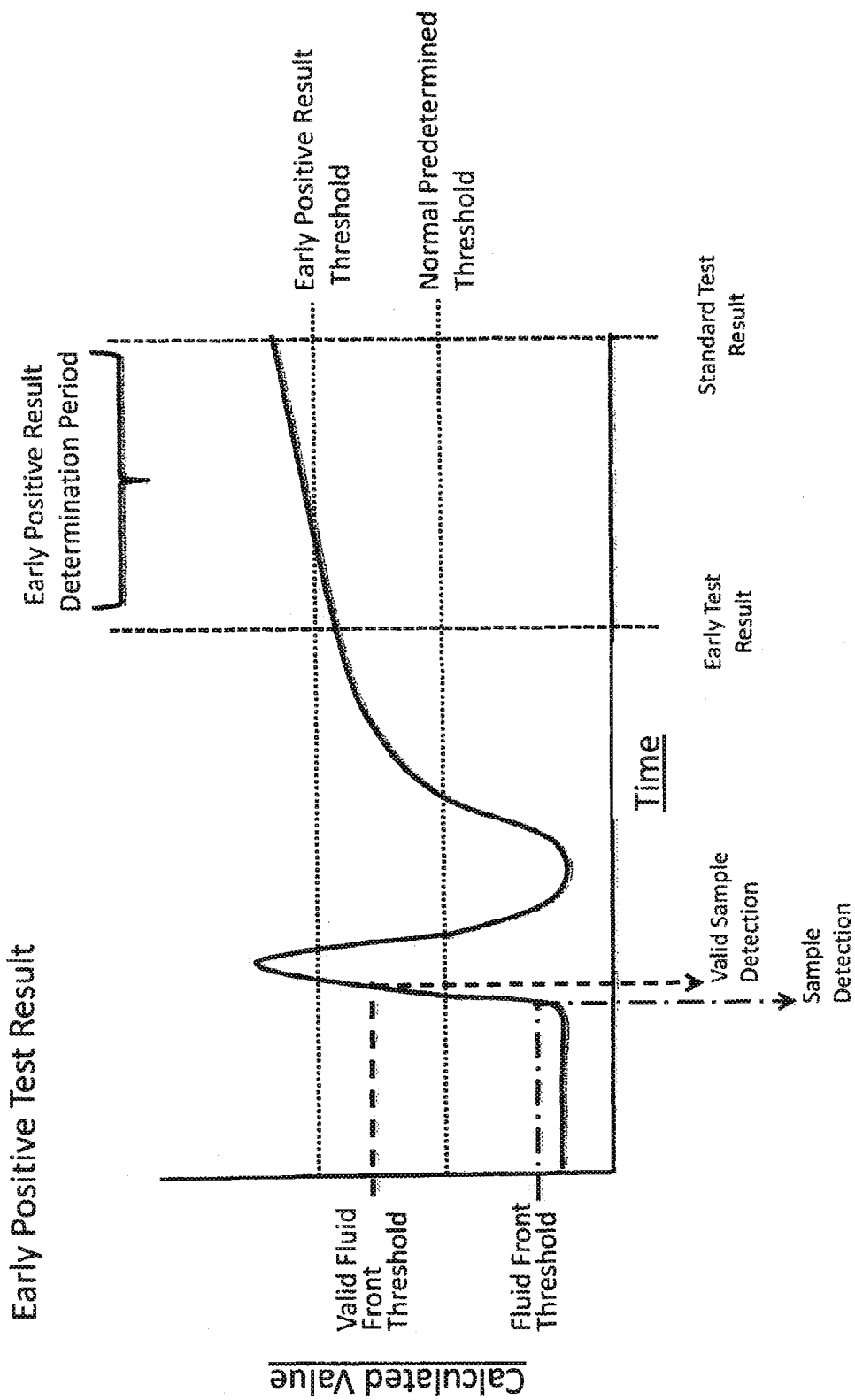

FIGS. 17A-C show graphical representations of typical readings (i.e. calculated values) against time of a testing cycle following device activation and sample application. In FIGS. 17A-C, a calculated value exceeding a fluid front threshold indicates that a fluid sample has been detected. Subsequently thereafter, a calculated value exceeding a valid fluid front threshold indicates that a valid sample has been detected and the device is operating. The calculated signal then drops and levels off. At this point in the testing cycle, the calculated signal may resemble one of the three graphs illustrated in FIGS. 17A-C. FIG. 17A illustrates a positive test result occurring at the standard test result time period when the calculated value exceeds the normal predetermined threshold value but is below the early positive result threshold value. FIG. 17B illustrates a negative result occurring at the standard test result time period when the calculated value is below the normal predetermined threshold value. FIG. 17C illustrates an early positive result occurring anytime between the early positive test result time period and the standard test result time period when the calculated value exceeds the early positive result threshold value.

In some preferred embodiments, device 10 may also have a logger system configured to download critical data from the microcontroller during prepackage testing or post use testing. The capability to download data is critical especially for trouble-shooting and product development purposes. Additionally, this logger system can be used during manufacturing as a quality control tool.

EXPERIMENTAL

The performance of finished devices was verified and validated through a series of studies summarized as follows:

Analytical Sensitivity

Fifty (50) devices were tested to determine the endpoint sensitivity and general functionality. Devices were dipped such that the sample receiving member was submerged in an hCG standard prepared in pooled negative urine for 5 seconds. Specifically, ten (10) devices were dipped in 0 mIU/mL and 5 mIU/mL of hCG standard, respectively, and fifteen devices (15) were dipped in 10 mIU/mL and 20 mIU/mL of hCG standard, respectively. The results summarized in Table 1 illustrate that a positive result is consistently produced in devices tested in standards with an hCG concentration of 10 mIU/mL and above.

TABLE 1

Analytical sensitivity

| hCG Std. | Displayed Result | Mean Time for Result (min:sec) |
| --- | --- | --- |
| 0 mIU/mL | 10/10 NO− | 3:28 (Range = 3:25-3:29) |
| 5 mIU/mL | 6/10 YES+ 4/10 NO− | 3:24 (Range = 3:21-3:25) |
| 10 mIU/mL | 14/15 YES+ 1/15 "?" (invalid) | 3:26 (Range = 3:25-3:36) |
| 20 mIU/mL | 15/15 YES+ | 3:27 (Range = 3:25-3:29) |

Verification of Device for Early Positive Response

Twenty (20) devices were tested to verify the ability of the device to produce a result from a positive urine sample earlier than the standard 3-minute result time. Devices were dipped in an hCG standard prepared in pooled negative urine as described above. Specifically, ten (10) devices were dipped in 10 mIU/mL of hCG standard, and five (5) devices were dipped in 100 mIU/mL and 10,000 mIU of hCG standard, respectively. The results summarized in Table 2 illustrate that a positive result is produced earlier than 3 minutes when devices were tested using standards with an hCG concentration of 100 mIU/mL and above.

TABLE 2

Early Positive Response

| hCG Std. | Displayed Result | Mean Time for Result (min:sec) |
| --- | --- | --- |
| 10 mIU/mL | 10/10 YES+ | 3:23 (Range = 3:21-3:26) |
| 100 mIU/mL | 5/5 YES+ | 1:53 (Range = 1:49-1:58) |
| 10,000 mIU/mL | 5/5 YES+ | 1:53 (Range = 1:51-1:56) |

Valid Fluid Front Testing

To obtain a valid (YES+/NO−) result, the device must detect a valid fluid front by sensing the presence of the label reagent (gold) in the sample as it passes through the detection zone. In the absence of sensing the presence of the label reagent the device will display a "?" invalid result. This invalid state can be simulated using test strips containing all the appropriate reagents but lacking the label reagent. Ten (10) functional devices employing test strips lacking the label reagent were dipped in an hCG standard prepared in pooled negative urine as described above. Specifically, five (5) devices were dipped in 0 mIU/mL and 100 mIU/mL of hCG standard, respectively. The results summarized in Table 3 illustrate that, in the absence of the label reagent, each of the devices yielded a "?" invalid result when tested with 0 mIU/mL and 100 mIU/mL of hCG standards.

TABLE 3

Valid fluid front testing using label-free test strips

| hCG Std. | Displayed Result | Mean Time for Result (min:sec) |
|---|---|---|
| 0 and 100 mIU/mL | 10/10 "?" (invalid) | 0:24 (Range = 0:22-0:26) |

User Testing

When excessive amount of sample is applied to the sample receiving member in midstream use, a situation referred to as "flooding" may occur where the label reagent is not released and therefore does not migrate due to rapid and total saturation of the test strip, or it is diluted by the rush of sample to a color level below the pre-established valid fluid front threshold. To test whether "flooding" occurs, thirty (30) devices were tested by midstream sample application using in-house non-pregnant volunteer users. The results summarized in Table 3 illustrates that a negative result "NO–" was produced in twenty-nine (29) devices, while one (1) device produced an invalid result ("?") soon after sample application. The device with the invalid result was replaced with a new device and retested by the same volunteer. The new device produced "NO–" result during repeat testing for an overall accuracy of 100%. Electronic data extracted from the device that produced an invalid result "?" identified that the cause of the invalid result was due to the migration of the label (gold) not meeting the valid fluid front threshold.

TABLE 4

User testing (midstream sample application)

| Sample | Displayed Result | Test Strip Result | Mean Sample Weight (g) |
|---|---|---|---|
| midstream urine (non-pregnant) | 29/30 NO–<br>1/30 "?"<br>Repeat testing of invalid<br>1/1 NO– | 31/31 negative | 1.10 (range 0.87-1.36) |

While one or more preferred embodiments of the invention are described above, it should be appreciated by those skilled in the art that various modifications and variations can be made in the present invention without departing from the scope and spirit thereof. It is intended that the present invention cover such modifications and variations as come within the scope and spirit of the appended claims and their equivalents.

We claim:

1. A diagnostic device for detecting the presence of an analyte in a fluid sample, the device comprising:
   a. a casing having a display;
   b. a test strip mounted in said casing, said test strip having a length and a width and a test result site located thereon;
   c. a light shield mounted in said casing adjacent said test strip, said light shield having at least two through holes formed therein;
   d. a processor mounted in said casing;
   e. a sensor mounted in said casing adjacent one of said at least two through holes, said sensor being operatively coupled to said processor;
   f. a light source mounted in said casing adjacent to the other of said at least two through holes, said light source being operatively coupled to said processor;
   wherein a portion of said light shield is configured to exert pressure across said width of said test strip to inhibit uneven fluid channeling along said length of said test strip.

2. The device of claim 1, further comprising a second sensor mounted in said casing adjacent to one of said at least two through holes with said sensor, said second sensor being operatively coupled to said processor, wherein a derivative is calculated by subtracting a signal from one of said sensor and said second sensor from a signal of the other of said sensor and said second sensor.

3. The device of claim 2, wherein
   a. said processor is configured to receive a signal froth said sensors; and
   b. when said derivative of said signal reading from said sensors is greater than an early positive result threshold value at any time after a predetermined time period, said processor is configured to display a positive result message on said display.

4. The device of claim 3, wherein said early positive result threshold value is greater than a normal predetermined threshold value, and said predetermined time period is less than a standard time period.

\* \* \* \* \*